(12) United States Patent
Nishimura

(10) Patent No.: US 7,455,449 B2
(45) Date of Patent: Nov. 25, 2008

(54) DIFFERENTIAL SCANNING CALORIMETER

(75) Inventor: Shinya Nishimura, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 136 days.

(21) Appl. No.: 11/657,271

(22) Filed: Jan. 24, 2007

(65) Prior Publication Data

US 2007/0189357 A1 Aug. 16, 2007

(30) Foreign Application Priority Data

Jan. 27, 2006 (JP) .............................. 2006-019122

(51) Int. Cl.
*G01N 25/20* (2006.01)
(52) U.S. Cl. .............................. 374/12; 374/10; 374/31; 374/112
(58) Field of Classification Search ............. 374/10–13, 374/31–42, 112–113, 166
See application file for complete search history.

(56) References Cited

U.S. PATENT DOCUMENTS

| 3,267,728 | A | * | 8/1966 | Solomons ..................... 374/34 |
| 3,384,819 | A | * | 5/1968 | Rinkel .......................... 324/95 |
| 3,451,267 | A | * | 6/1969 | Wiegert et al. ................ 374/38 |
| 4,345,844 | A | * | 8/1982 | Birukoff ....................... 374/31 |
| 5,551,282 | A | * | 9/1996 | Vander Heyden .......... 73/30.03 |
| 6,146,013 | A | * | 11/2000 | Huetter et al. ................ 374/46 |
| 2008/0025364 | A1 | * | 1/2008 | Nakatani et al. .............. 374/12 |
| 2008/0151962 | A1 | * | 6/2008 | Teramoto ..................... 374/10 |

FOREIGN PATENT DOCUMENTS

| JP | H07-65974 B | 7/1995 |
| JP | H07-122619 B | 12/1995 |
| JP | 2005-83763 | 3/2005 |

* cited by examiner

*Primary Examiner*—Edward Lefkowitz
*Assistant Examiner*—Bret Adams
(74) *Attorney, Agent, or Firm*—Brinks Hofer Gilson & Lione

(57) ABSTRACT

There is provided a differential scanning calorimeter possessing an accommodation chamber accommodating a sample to be measured and a reference material, a heater heating the accommodation chamber, a differential heat flow detector outputting a temperature difference between the sample to be measured and the reference material as a heat flow difference signal, a cooling block cooling-controlled to a predetermined temperature, a heat resistor which mechanically connects the cooling block and the accommodation chamber and forms a heat flow path between both, a first fixation means which fixes the heat resistor to the cooling block by pressing the former while being biased by a constant elastic force, and a second fixation means which fixes the accommodation chamber to the heat resistor by pressing the former while being biased by a constant elastic force.

6 Claims, 2 Drawing Sheets

DIFFERENTIAL SCANNING CALORIMETER

This application claims priority under 35 U.S.C. §119 to Japanese Patent Application Nos. JP2006-019122 filed Jan. 27, 2006, the entire content of which is hereby incorporated by reference.

BACKGROUND OF THE INVENTION

The present invention is one relating to a thermal analysis apparatus measuring how physical properties of a sample change along with a temperature. Especially, it is one relating to a differential scanning calorimeter which, when the temperature has been changed, measures a heat quantity, that the sample excessively radiates or absorbs in comparison with a reference material, on the basis of a temperature difference (differential heat) between the sample and the reference material.

The differential scanning calorimeter is an apparatus which, when the sample and the reference material (thermally stable material, e.g., alumina and the like) have been disposed while being juxtaposed and temperatures of both have been changed at a constant rate, differentially detects the heat quantity that the sample excessively radiates or absorbs in comparison with the reference material.

As to this kind of apparatus, although various ones are provided, as one of them, there is known one having a cooling mechanism which not only heats the temperature of an accommodation chamber accommodating the sample and the reference material but also cools it.

For example, there is known one having a cooling device (electric cooling device) in which a coolant is supplied to a periphery of a heating furnace which heats the sample, thereby cooling a periphery of the sample through the heating furnace (e.g., JP-B-7-65974).

Further, as other apparatus, there is also known one having a cooling device (gas cooling device) in which a very low (e.g., −196° C.) gas obtained by evaporating a liquefied nitrogen and the like is supplied into a sample chamber (accommodation chamber) accommodating the sample, thereby cooling a sample chamber inside (e.g., JP-B-7-122619).

Additionally, there is also known one in which there are used in combination a gas cooling device performing the cooling by the very low temperature gas obtained by evaporating the liquefied nitrogen and the like, and an electric cooling device performing the cooling by compressing the coolant by a compressor and adiabatically expanding it, thereby cooling a heat sink (accommodation chamber) accommodating the sample (e.g., JP-A-2005-83763).

Like this, the differential scanning calorimeter performs an analysis of the sample under various temperature conditions by freely controlling the temperature by the cooling devices of various kinds.

However, in the above conventional methods, the following problems are left.

That is, in the differential scanning calorimeter having the cooling device, a heat flow path that is a flow passage of a heat is secured by mechanically connecting the accommodation chamber, e.g., the heat sink, accommodating the sample and the cooling device. This is for efficiently heating and cooling the heat sink.

However, the heat sink and the cooling device are not made by a material of completely the same quality, but generally are respectively made by utilizing materials of different qualities. In other words, the heat flow path is formed by mechanically connecting metals of different kinds to each other. Therefore, when analyzing the sample, if the heating and the cooling are repeatedly performed, a distortion, a deviation and the like have occurred in a joint face due to a difference in thermal expansion coefficient. As a result, a flow of the heat changes midway, so that there has existed a possibility that it is impossible to accurately perform the analysis of the sample. Further, since the distortion and the deviation change every moment in compliance with conditions at that time, a reproducibility is bad, and it has been impossible to collect a measurement result and the like.

The present invention is one having been made in view of the circumstances like this, and its object is to provide a differential scanning calorimeter in which, even if the heating or the cooling has been repeatedly performed, it is possible to maintain a stable heat flow path, and which can highly precisely perform a measurement of the sample to be measured.

SUMMARY OF THE INVENTION

In order to solve the above problems, the present invention provides the following means.

A differential scanning calorimeter of the present invention is one characterized by possessing an accommodation chamber accommodating therein a sample to be measured and a reference material, a heater attached so as to surround a periphery of the accommodation chamber to thereby heat the accommodation chamber, a differential heat flow detector which is provided in the accommodation chamber, detects a temperature difference between the sample to be measured and the reference material, and outputs the temperature difference having been detected as a heat flow difference signal, a cooling block which is disposed below the accommodation chamber while being separated by a constant distance, and cooling-controlled to a predetermined temperature, a heat resistor which is formed so as to have a predetermined heat resistance, interposed between the cooling block and the accommodation chamber to thereby mechanically connect both, and forms a heat flow path between the cooling block and the accommodation chamber, a support means supporting the cooling block, and a fixation means of at least any one between a first fixation means which fixes the heat resistor to the cooling block by pressing the former while being biased by a constant elastic force, and a second fixation means which fixes the accommodation chamber to the heat resistor by pressing the former while being biased by a constant elastic force.

In the differential scanning calorimeter concerned with this invention, since it has the heater and the cooling block, by heating or cooling an object article to be measured and the reference material, which have been accommodated in the accommodation chamber, a desired temperature can be easily produced. And, the differential heat flow detector detects the temperature difference between the sample to be measured and the reference material when the temperature in the accommodation chamber has been changed, and outputs the temperature difference having been detected as the heat flow difference signal. By obtaining this heat flow difference signal, a heat quantity that the sample to be measured excessively radiates or absorbs with respect to the reference material can be differentially detected, so that it is possible to perform a thermal analysis of the sample to be measured.

Here, in a case where the heater has been operated, the accommodation chamber is directly heated and the temperature of its inside rises, and the temperatures of the sample to be measured and the reference material, which are accommodated, rise. Further, this heat is transmitted from the accommodation chamber to the cooling block while passing through the heat resistor. In other words, the heat resistor becomes the flow passage, i.e., the heat flow path, of the heat flowing between the accommodation chamber and the cooling block. Further, in a case where the cooling block having been supported by the support means has been cooled to a predetermined temperature (e.g., about −190° C.), since the heat is efficiently heat-exchanged, it is possible to rapidly cool the sample to be measured and the reference material, which are accommodated in the accommodation chamber. Like this, by opportunely performing the heating and the cooling, it is possible to widen a temperature range, and there can be made a desired temperature condition in a short time.

Especially, if the heating and the cooling are repeated, it follows that the accommodation chamber, the heat resistor and the cooling block respectively repeat an expansion and a contraction. On this occasion, since the accommodation chamber, the heat resistor and the cooling block generally differ respectively in their thermal expansion coefficients, there occur a distortion, a positional deviation and the like in a mutual joint face, i.e., a joint face between the heat resistor and the accommodation chamber, and a joint face between the heat resistor and the cooling block.

However, since there is possessed the fixation means of at least any one of the first fixation means or the second fixation means, it is possible to nullify the defect resulting from the distortion, the positional deviation and the like, which have been mentioned above. That is, in a case where there has been possessed the first fixation means, the heat resistor is fixed under a state having been pressed to the cooling block while being biased by a constant elastic force. Therefore, by the difference in thermal expansion coefficient between the heat resistor and the cooling block, even if the heat resistor is distorted with respect to the cooling block or the positional deviation and the like occur, it is possible to buffer a stress resulting from these by the elastic force. In other words, by absorbing the stress resulting from the distortion and the like by the elastic force, a fixation state between the cooling block and the heat resistor can be always maintained to a constant state.

Further, in a case where there has been possessed the second fixation means, the accommodation chamber is fixed under a state having been pressed to the heat resistor while being biased by a constant elastic force. Therefore, by the difference in thermal expansion coefficient between the accommodation chamber and the heat resistor, even if the heat resistor is distorted with respect to the accommodation chamber or the positional deviation and the like occur, it is possible to buffer a stress resulting from these by the elastic force. Therefore, similarly, a fixation state between the accommodation chamber and the heat resistor can be always maintained to a constant state.

Like this, since there is possessed the fixation means of at least any one, even if the heating and the cooling are repeated, differing from conventional one, it is possible to always stably maintain the heat flow path of at least any one of between the heat resistor and the accommodation chamber or between the heat resistor and the cooling block. As a result, it is possible to certainly obtain a heat flow difference signal having the reproducibility. Therefore, it is possible to highly precisely measure the sample to be measured, and the reliability can be improved.

Incidentally, it is desirable to simultaneously possess both the fixation means.

Further, a differential scanning calorimeter of the present invention is one characterized in that, in the above differential scanning calorimeter of the present invention, the first fixation means possesses a through-hole penetrating an upper face and a lower face of the cooling block, a shaft body which is movably inserted into the through-hole, whose one end is fixed to the heat resistor, and whose other end protrudes to an outward from an inside of the through-hole, a nut meshed with the other end side of the shaft body, and a coil spring which is covered to the shaft body so as to surround a periphery of the shaft body under a state having been nipped between the meshing body and the cooling block, and biases the shaft body toward the other end side by an elastic force, and the elastic force of the coil spring is made adjustable by moving the nut by a mesh in an axial direction of the shaft body.

In the differential scanning calorimeter concerned with this invention, the heat resistor and the cooling block are connection-fixed through the shaft body. On this occasion, since the coil spring is disposed between the lower face of the cooling block and the nut, the elastic force of the coil spring is transmitted to the shaft body movable in the through-hole through the nut. By this, the shaft body becomes a state being always biased toward the other end side. Further, as to this elastic force, it is possible to perform an adjustment because a compression amount of the coil spring changes by moving the nut by a mesh in a axial direction of the shaft body. As a result, it is possible to previously adjust the elastic force of the coil spring to a constant elastic force.

Like this, since the shaft body is biased toward the other end side, the heat resistor fixed to one end side of the shaft body is pulled to the cooling block side. By this, the heat resistor is pressed and fixed to the cooling block while being biased by the constant elastic force.

And, by repetitions of the heating and the cooling, even if the heat resistor distorts with respect to the cooling block or the positional deviation and the like occur, the coil spring expands or contracts in compliance with them, thereby absorbing the stress resulting from the distortion and the like. Therefore, a fixation state between the heat resistor and the cooling block can be made constant, so that it is possible to stabilize the heat flow path.

Especially, since the first fixation means can be constituted by the coil spring, the shaft body, the nut and the like without using a special mechanism, it is possible to intend to simplify the constitution and reduce a cost.

A differential scanning calorimeter concerned with this invention is one characterized in that, in the above differential scanning calorimeter of the present invention, the coil spring is formed by a material made of a heat-resistant alloy.

In the differential scanning calorimeter concerned with this invention, since the coil spring is the heat-resistant alloy, e.g., nickel base heat-resistant alloy such as inconel, even if the temperature itself of the cooling block has raised to about 400° C. for instance, there is no fact that a mechanical property changes by the heat. Therefore, it is possible to bias the heat resistor by a predetermined elastic force, and the reliability can be raised.

Further, a differential scanning calorimeter of the present invention is one characterized in that, in the above differential scanning calorimeter of the present invention, an annular bushing comprising ceramic is covered to the shaft body so as to surround the periphery of the shaft body under a state having been nipped between the coil spring and the cooling block.

In the differential scanning calorimeter concerned with this invention, since the bushing intervenes between the coil spring and the cooling block, there is no fact that the coil spring directly contacts with the cooling block. In other words, there is no fact that the heat is directly transmitted from the cooling block to the coil spring, so that it is possible to prevent a temperature rise of the coil spring as much as possible. Therefore, it is possible to more certainly prevent the change in mechanical property of the coil spring by an excessive heat. Further, since a heat influence on the coil spring can be reduced as much as possible, it is possible to increase a selectivity of a material.

Further, a differential scanning calorimeter of the present invention is one characterized in that, in any of the above differential scanning calorimeters of the present invention, the second fixation means possesses an opening having been formed in the heat resistor, a second through-hole penetrating an upper face and a lower face of the cooling block, and a second coil spring which is movably inserted into both the opening and the second through-hole, whose one end is fixed to the accommodation chamber, and whose the other end is fixed to the support means, thereby biasing the accommodation chamber toward the heat resistor by an elastic force, and the second coil spring is fixed to the support means such that its own elastic force is adjustable.

In the differential scanning calorimeter concerned with this invention, the accommodation chamber and the support means are connection-fixed through the second coil spring which is movably inserted into the opening and the second through-hole. On this occasion, the coil spring pulls the accommodation chamber. Therefore, the accommodation chamber is pressed and fixed to the heat resistor while being biased by a constant elastic force. Incidentally, since the second coil spring is fixed to the support means such that its own elastic force is adjustable, it is possible to previously adjust to the constant elastic force. And, by repetitions of the heating and the cooling, even if the heat resistor distorts with respect to the accommodation chamber or the positional deviation and the like occur, the second coil spring expands or contracts in compliance with them, thereby absorbing the stress resulting from the distortion and the like. Therefore, the fixation state between the accommodation chamber and the heat resistor can be made constant, and it is possible to stabilize the heat flow path.

Further, since the second fixation means can be constituted by the coil spring and the like without using the special mechanism, it is possible to intend to simplify the constitution and reduce the cost.

Further, a differential scanning calorimeter of the present invention is one characterized in that, in the above differential scanning calorimeter of the present invention, the accommodation chamber and the coil spring are fixed through a wire material having a heat resistance, and between the accommodation chamber and the coil spring there is separated by a predetermined distance.

In the differential scanning calorimeter concerned with this invention, since the second coil spring is connected to the accommodation chamber through the wire material, a distance between the second coil spring and the accommodation chamber is separated by a constant distance. Therefore, even if the temperature of the accommodation chamber directly heated by the heater has raised to about 700° C. for instance, there is no fact that this heat is directly transmitted to the second coil spring, so that a temperature rise of the second coil spring can be prevented as much as possible. Therefore, it is possible to prevent a change in mechanical property of the second coil spring by the excessive heat. As a result, it is possible to bias the accommodation chamber toward the heat resistor by a predetermined elastic force, and the reliability can be improved.

According to the differential scanning calorimeter concerned with the present invention, even if the heating and the cooling have been repeated, since it is possible to always stably maintain the heat flow path of at least any one of between the heat resistor and the accommodation chamber or between the heat resistor and the cooling block, it is possible to certainly obtain the heat flow difference signal having the reproducibility. Therefore, it is possible to highly precisely measure the sample to be measured, and the reliability can be improved.

DETAILED DESCRIPTION OF THE PREFERRED EMBODIMENTS

Figure 1:
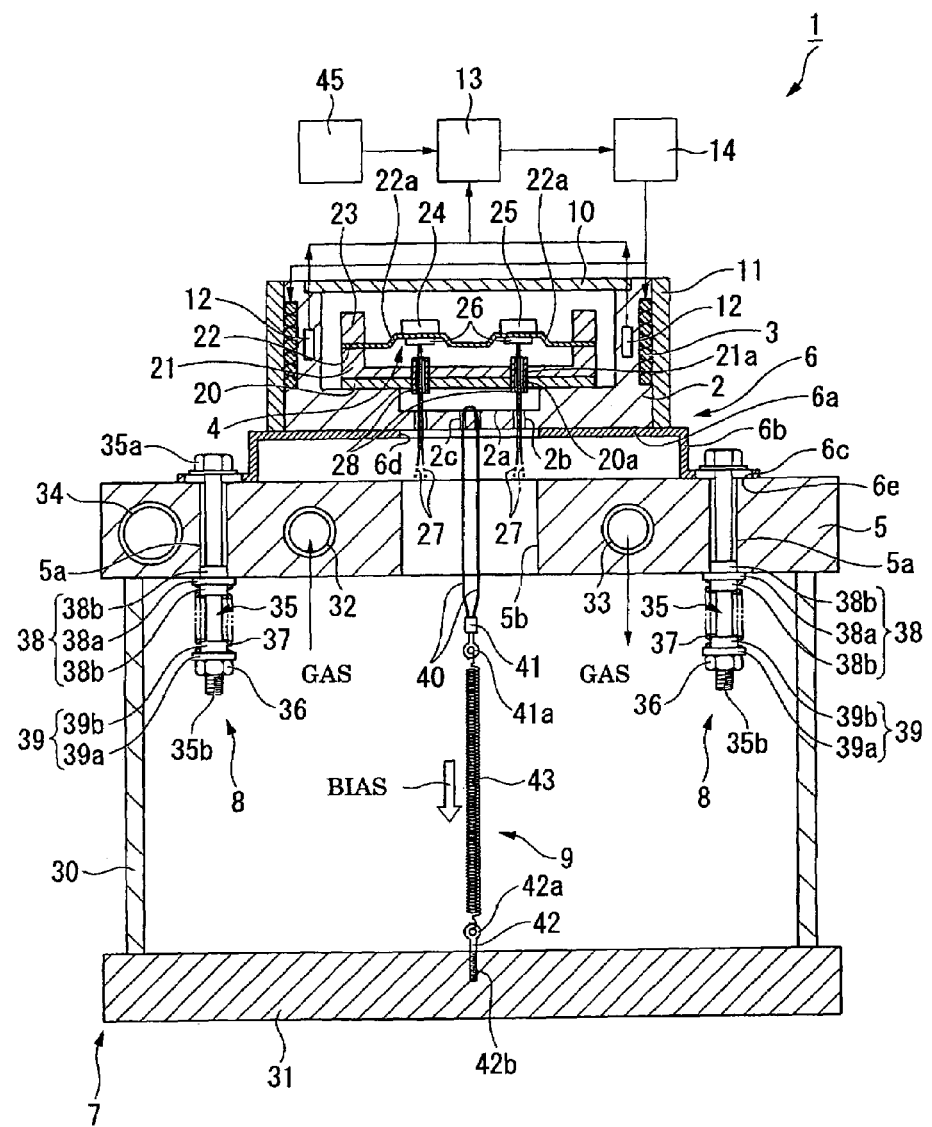
FIG. 1 is a constitution view showing one embodiment of a differential scanning calorimeter concerned with the present invention.
Figure 2:
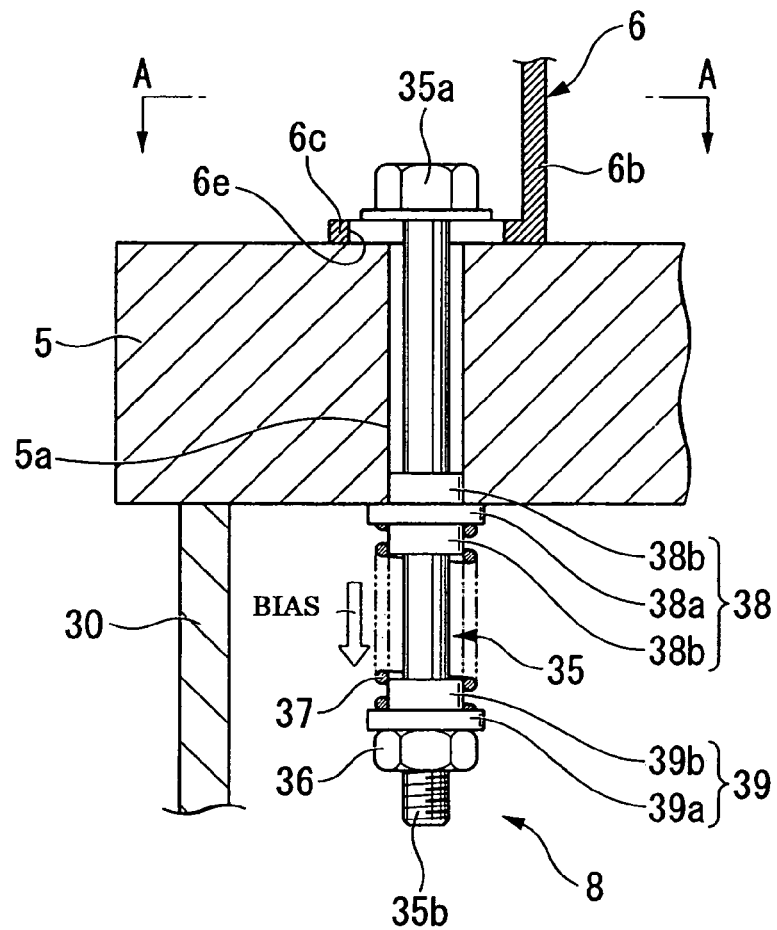
FIG. 2 is an enlarged view of a first fixation means constituting the differential scanning calorimeter shown in FIG. 1.
Figure 3:
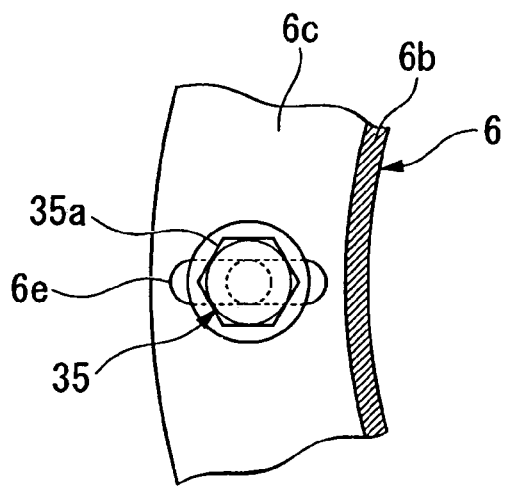
FIG. 3 is a sectional view seen along an arrow A-A shown in FIG. 2.

Hereunder, one embodiment of a differential scanning calorimeter concerned with the present invention is explained by referring to FIG. 1 to FIG. 3.

As shown in FIG. 1, a differential scanning calorimeter 1 of the present embodiment possesses a heat sink (accommodation chamber) 2 accommodating therein a sample to be measured and a reference material (both not shown in the drawing), a heater 3 attached so as to surround a periphery of the heat sink 2 and heating the heat sink 2, a differential heat flow detector 4 which is provided in the heat sink 2, detects a temperature difference between the sample to be measured and the reference material, and outputs the detected temperature difference as a heat flow difference signal, a cooling block 5 which is disposed below the heat sink 2 while being spaced by a certain distance, and cooling-controlled to a predetermined temperature, a heat resistor 6 which is formed so as to have a predetermined heat resistance, interposed between the cooling block 5 and the heat sink 2 to thereby mechanically connect both, and forms a heat flow path between the cooling block 5 and the heat sink 2, a support means 7 supporting the cooling block 5, a first fixation means 8 fixing the heat resistor 6 to the cooling block 5 by pressing the former while being biased by a constant elastic force, and a second fixation means 9 fixing the heat sink 2 to the heat resistor 6 by pressing the former while being biased by a constant elastic force.

The heat sink 2 is formed like a cylinder, and adapted such that its inside is sealed by a detachable lid 10 except a small hole for a purge gas exhaust, which is not shown in the drawing. Like this, by preventing an outside air from freely entering into an inside, a soaking is contrived by suppressing a temperature fluctuation due to convection. Further, the heat sink 2 and the lid 10 are made of pure silver or the like excellent in its high heat conductivity so as to equally supply the heat flow from the heater 3 and the cooling block 5 to the sample to be measured and the reference material. Incidentally, the pure silver can be used in a range of from −150° C. to +725° C. for instance.

Further, the heater 3 with an insulation coating is wound around an outer periphery of the heat sink 2. Additionally, a cover 11 made of stainless for instance is attached so as to cover a periphery of this heater 3. The heater 3 is protected by this cover 11.

Further, there is adapted such that a control thermocouple 12 measuring a temperature of the heat sink 2 is attached to a side face of the heat sink 2, and the temperature of the seat sink 2 having been measured is outputted to a PID arithmetic and control section 13 while being converted into a temperature signal. Further, there is adapted such that the heater 3 is connected to an electric power supply section 14, and performs a heating on the basis of an output designation from the electric power supply section 14. About the PID arithmetic and control section 13 and the electric power supply section 14, detailed description is given later.

In the heat sink 2, a heat buffer plate 20 is mounted so as to close a concavity 2a having been formed in an approximate center of its bottom face. This heat buffer plate 20 is made of, e.g., inconel whose heat resistance is high and whose heat conductivity is low in comparison with the silver, and the like. Further, onto the heat buffer plate 20, there is mounted a lower side holding plate 21 having been formed like a cup by, e.g., the silver and the like. In the lower side holding plate 21, there is mounted an upper side holding plate 23 having been annularly formed by, e.g., the silver and the like under a state that a heat transfer plate 22 has been nipped between them. The upper side holding plate 23, the heat transfer plate 22, the lower side holding plate 21 and the heat buffer plate 20 are monolithically fixed to the heat sink 2 by screws not shown in the drawing, and the like. As to each of the lower side holding plate 21 and the upper side holding plate 23, its outer periphery is formed in a circular shape, and its inner periphery is bored in an elliptic shape.

Further, in each of the lower side holding plate 21 and the heat buffer plate 20, two openings 20a, 21a are respectively formed in its approximate center. Further, also in the concavity 2a of the heat sink 2, two openings 2b are similarly formed in its approximate center, and additionally two minute openings 2c are formed inside these openings 2b.

The heat transfer plate 22 is a plate made of constantan for instance, and brazed by a silver solder and the like under a state in which its peripheral edge has been nipped between the lower side holding plate 21 and the upper side holding plate 23. In an approximate center of this heat transfer plate 22, two convex parts 22a are symmetrically provided. And, onto these two convex parts 22a, there are mounted a sample holder 24 and a reference material holder 25, which accommodate respectively the sample to be measured and the reference material.

Further, to lower faces of the two convex parts 22a, chromel plates 26 are respectively fixed by, e.g., a spot welding and the like. Thermocouple fine lines 27 are welded to these chromel plates 26. And, the chromel plates 26 output a temperature difference between the sample to be measured and the reference material, which has been detected, to an outside as a heat flow difference signal through the thermocouple fine lines 27. That is, the chromel plates 26, the heat transfer plate 22 and the thermocouple fine lines 27 constitute the above differential heat flow detector 4.

Further, the thermocouple fine lines 27 are drawn out to an outside of the heat sink 2 through the opening 2b having been formed in the concavity 2a after once having been drawn out into the concavity 2a of the heat sink 2 through a two-core insulation tube 28 having been inserted into the openings 20a and 21a of the heat buffer plate 20 and the lower side holding plate 21.

The heat sink 2 is mounted onto the cooling block 5 through the heat resistor 6. This heat resistor 6 is formed like a hat in section. That is, the heat resistor 6 is constituted by a disc-like top plate 6a on which the heat sink 2 is mounted, a peripheral wall part 6b of a circular shape in section, which has been bent approximately at 90 degrees from a peripheral edge of the top plate 6a, and an annular flange part 6c having been additionally bent approximately at 90 degrees from the peripheral wall part 6b. Further, an opening 6d is formed in a center of the top plate 6a.

Additionally, in this heat resistor 6, there are formed four slits not shown in the drawing at every 90 degrees toward a peripheral direction from a vicinity of the peripheral edge of the top plate 6a to the peripheral wall part 6b and the flange part 6c. By this, the peripheral wall part 6b and the flange part 6c become states in which they are divided into four in the peripheral direction.

Further, as shown in FIG. 2 and FIG. 3, in the flange part 6c having been divided into four, there is formed an opening 6e through which a long screw (shaft body) 35 mentioned later is respectively inserted. Incidentally, this opening 6e is formed in a long hole toward a radial direction of the heat resistor 6.

Further, the heat resistor 6 of the present embodiment is made by a stainless alloy. Here, in which there is a case where the cooling block 5 employs the electric cooling system performing the cooling by compressing the coolant by the compressor and adiabatically expanding the coolant. In this case, it needs to be contrived to widen a measurable temperature range. Further, although the heat resistor 6 becomes a path of the heat flow toward the cooling block 5 from the heat sink 2, a heat resistance value of the heat resistor 6 is determined from a sectional area and a distance of this path and a heat conductivity of a material. If this heat resistance value is too large, a heating efficiency of the heat sink 2 is good but a cooling efficiency becomes deteriorated. Further, if the heat resistance value is too small, there becomes a reverse of the former. Therefore, the heat resistor 6 is designed so as to become a heat resistance value which is good in balance.

The cooling block 5 is formed such that its external shape becomes like a cuboid under a state having a space in its inside, and mounted onto a base 31 by four supporting columns 30 having been fixed to four corners. That is, the supporting columns 30 and the base 31 constitute the above support means 7.

Incidentally, in order to cause the heat to equally flow to the heat resistor 6 and the heat sink 2, it is desirable that the cooling block 5 is made by a high heat conductivity material. Further, since a temperature rising/lowering rate of the heat sink 2 becomes also one of important performances for the differential scanning calorimeter, it is desirable that a heat capacity of the cooling block 5 itself is also small. In addition to these reasons, in the present embodiment, the cooling block 5 is made by pure aluminum from a comprehensive stand point of the price, the heat resistance and the like.

As having been mentioned above, the heat sink 2, the heat resistor 6 and the cooling block 5 are made by the metals different in kinds, whose thermal expansion coefficients are respectively different.

In a side face of the cooling block 5, there are formed a gas supply port 32 supplying a very low temperature gas obtained by evaporating the liquefied nitrogen to the space of the inside, and a gas discharge port 33 discharging the gas after having been heat-exchanged in the space of the inside. Additionally, in the side face of the cooling block 5, in addition to the gas supply port 32 and the gas discharge port 33, there is formed also an insertion port 34 for a cooling head of an electric cooler not shown in the drawing.

In other words, this cooling block 5 is adapted so as to be cooling-controlled to a predetermined temperature (e.g., in a range of from −90° C. to −190° C.) by two systems of a gas cooling system in which the cooling is performed by the very low temperature gas, and an electric cooling system in which the cooling is performed by compressing and adiabatically expanding the coolant by the compressor.

Further, as shown in FIG. 1, in the cooling block 5, four through-holes 5a penetrating an upper face and a lower face are formed in four corners, and a through-hole (second through-hole) 5b whose diameter is larger than the through-hole 5a is formed in a center. As shown in FIG. 1 and FIG. 2, in the four through-holes 5a, there is movably inserted a long screw 35 having a head part 35a in its one end. This long screw 35 is inserted through the opening 6e of the heat resistor 6 and the through-hole 5a such that the head part 35a is placed in the heat resistor 6 side, and the other end is formed in a length protruding to an outside of the cooling block 5. Further, the other end of the long screw 35 is made a thread part 35b having been threaded, and there is made such that a nut 36 is meshed.

Further, a coil spring 37 is covered to the long screw 35 under a state having been nipped between the nut 36 and the cooling block 5 so as to surround a periphery of the long screw 35. This coil spring 37 is made of the inconel of a nickel base heat-resisting alloy that is a heat-resisting alloy material. And, the coil spring 37 always biases the long screw 35 toward the other end side by its elastic force. By this, since the heat resistor 6 is pulled by the long screw 35 through the head part 35a, it is pressed to the cooling block 5 by a constant elastic force.

Incidentally, there is adapted such that a compressed quantity of the coil spring 37 can be changed by moving the nut 36 in an axial direction of the long screw 35 by a mesh, so that it is possible to adjust the elastic force of the coil spring 37.

Further, an annular bushing 38 comprising ceramic is covered to the long screw 35 under a state having been nipped between the coil spring 37 and the cooling block 5 so as to surround the periphery of the long screw 35. This bushing 38 is monolithically constituted, e.g., by a large diameter part 38a and two diameter-reduced parts 38b having been formed in both sides of the large diameter part 38a while nipping it. One diameter-reduced part 38b is inserted into the through-hole 5a of the cooling block 5, thereby stably supporting the long screw 35. Further, the other diameter-reduced part 38b is inserted into an inside of the coil spring 37, thereby stably supporting the coil spring 37. Further, the large diameter part 38a is formed in a diameter of a size larger than an outer diameter of the coil spring 37 and an inner diameter of the through-hole 5a, thereby positioning the bushing 38 and certainly butting the coil spring 37.

Additionally, similarly to the bushing 38 having been mentioned above, an annular bushing 39 surrounding the periphery of the long screw 35 is covered to the other end of the long screw 35 under a state having been nipped between the coil spring 37 and the nut 36. This bushing 39 is monolithically constituted by a large diameter part 39a and one diameter-reduced part 39b, and attached such that the large diameter part 39a is placed in the nut 36 side. And, the diameter-reduced part 39b is inserted into the inside of the coil spring 37, thereby stably supporting the coil spring 37.

The through-hole 5a, the long screw 35, the nut 36, the coil spring 37 and the bushings 38, 39, which have been mentioned above, constitute the above first fixation means 8.

Further, a wire (wire material) 40 made of the inconel having a heat resistance is movably passed to the through-hole 5b of the cooling block 5 and the opening 6d of the heat resistor 6, and one end side is fixed to the heat sink 2 and the other end side is connected to a fixation fitting 41 between the cooling block 5 and the base 31. This wire 41 is fixed at the fixation fitting 41 after entering into the heat sink 2 through one minute opening 2c having been formed in the heat sink 2 from the fixation fitting 41 and going out to an outside of the heat sink 2 through the other minute opening 2c. In other words, it is fixed under a state in which its looped tip has caught the heat sink 2.

Further, as to the fixation fitting 41, a tip part 41a in a side opposite to the base 31 is made a hook shape. Further, also on the base 31, there is provided a fixation fitting 42 having a tip part 42a of the hook shape similarly to the fixation fitting 41. This fixation fitting 42 is made in its base end part into a thread part 42b having been threaded, and fixed by a mesh with a tread groove having been formed in the base 31.

And, both the fixation fittings 41, 42 are connected through a coil spring (second coil spring) 43 having been detachably fixed to the respective tip parts 41a, 42a. This coil spring 43 is movably inserted through the through-hole 5b of the cooling block 5 and the opening 6d of the heat resistor 6. Further, between the coil spring 43 and the heat sink 2, there becomes a state having been separated by a predetermined distance by the wire 40.

The coil spring 43 always biases the heat sink 2 toward the heat resistor 6 by the elastic force through the wire 40. By this, since the heat sink 2 is pulled by the coil spring 43, it is pressed to the heat resistor 6 by a constant elastic force. Incidentally, there is adapted such that a compressed quantity of the coil spring 43 can be changed by changing a threaded quantity of the fixation fitting 42 having been meshed with the base 31, so that it is possible to freely adjust the elastic force of the coil spring 43.

The above PID arithmetic and control section 13 is connected to a temperature program setting instrument 45, in addition to the above-mentioned control thermocouple 12. The temperature program setting instrument 45 performs a program setting on the basis of an arbitrary temperature program having been inputted by a measuring person, and outputs a temperature signal having been set to the PID arithmetic and control section 13. And, the PID arithmetic and control section 13 performs a PID (proportion, differential, integration) operation from a difference between the temperature signal having been outputted from temperature program setting instrument 45 and a temperature signal having been outputted from the control thermocouple 13, thereby sending a signal to the electric power supply section 14 so as to bring out a suitable heater power output. And, there is adapted such that the electric power supply section 14 receives this signal, thereby supplying the electric power to the heater 3. By this, there is adapted such that the heat sink 2 is precisely temperature-controlled by a feedback loop of the PID operation.

Next, there is explained about a case where the thermal analysis of the sample to be measured is performed by the differential scanning calorimeter 1 having been constituted like this.

Since the differential scanning calorimeter 1 of the present invention possesses the heater 3 and the cooling block 5, it is possible to easily produce a desired temperature condition by heating or cooling the sample to be measured and the reference material, which have been seal-accommodated in the heat sink 2.

In the beginning, there is explained about a case where the heat sink 2 is heated by operating the heater 3. First, the measuring person inputs an arbitrary temperature program having been determined by oneself to the temperature program setting instrument 45. The temperature program setting instrument 45 outputs a temperature signal having been program-set on the basis of this inputted data to the PID arithmetic and control section 13. The PID arithmetic and control section 13 performs the PID operation from the difference between the temperature signal having been outputted from temperature program setting instrument 45 and the temperature signal having been outputted from the control thermocouple 13, thereby sending the signal to the electric power supply section 14 so as to bring out the suitable heater power output. By receiving this, the heater 3 operates, thereby starting to heat the heat sink 2.

The heat sink 2 is heated by the heater 3, and the temperature rises to about 700° C. for instance. This heat is transmitted to the sample holder 24 and the reference material holder 25 through the heat sink 2, the heat buffer plate 20, the lower side holding plate 21 and the heat transfer plate 22. As a result, the temperatures of the sample to be measured and the reference material, which are accommodated in the sample holder 24 and the reference material holder 25, rise as well. And, the differential heat flow detector 4 detects a temperature difference between the sample to be measures and the reference material, and outputs the temperature difference having been detected as a heat flow difference signal through the thermocouple fine lines 27. By obtaining this heat flow difference signal, it is possible to differentially detect the heat quantity that the sample to be measured excessively radiates or absorbs with respect to the reference material. As a result, it is possible to perform the thermal analysis of the sample to be measured. Especially, since the heat sink 2 is highly precisely temperature-controlled by a PID control as having been mentioned above, the thermal analysis can be accurately performed.

Here, one part of the heat of the heat sink 2 is transmitted to the cooling block 5 through the heat resistor 6, and heat-dissipated. In other words, the heat resistor 6 becomes a flow passage, i.e., the heat flow path, of the heat flowing between the heat sink 2 and the cooling block 5. On this occasion, the temperature of the flange part 6c of the heat resistor 6, i.e., the temperature of the joint face between the heat resistor 6 and the cooling block 5, becomes about 400° C. for instance.

Next, in a case where the cooling block 5 has been cooled to −190° C. for instance by the gas cooling system having utilized the very low temperature gas or the electric cooling system having utilized the coolant, since the heat of the heat sink 2 can be efficiently heat-exchanged, it is possible to rapidly cool the sample to be measured and the reference material, which are accommodated in the heat sink 2. In this case, if the heating of the heater 3 is stopped, it is possible to cool the heat sink 2 to about −160° C. for instance.

Like this, since the differential scanning calorimeter 1 of the present embodiment can solely or simultaneously perform the heating and the cooling, it is possible to make a measurement temperature range into a wide range, and it is possible to make a desired temperature condition in a short time.

Especially, if the heating and the cooling are repeated, it follows that the heat sink 2, the heat resistor 6 and the cooling block 5 respectively repeat an expansion/contraction. On this occasion, since the heat sink 2, the heat resistor 6 and the cooling block 5 are the metals of mutually different kinds, which have been formed respectively by the different materials, there occur the distortion, the positional deviation in, and the like in the mutual joint face, i.e., the joint face between the heat sink 2 and the heat resistor 6, and the joint face between the heat resistor 6 and the cooling block 5.

However, the heat resistor 6 in the present embodiment is fixed under the state having been pressed to the cooling block 5 while being biased by the constant elastic force by the first fixation means 8. Therefore, by a difference in thermal expansion coefficient between the heat resistor 6 and the cooling block 5, even if the heat resistor 6 has distorted with respect to the cooling block 5 or the positional deviation and the like have occurred, the stress resulting from these can be buffered by the elastic force. In other words, by absorbing the stress resulting from the distortion and the like by the elastic force, it is possible to always maintain a fixation state between the cooling block 5 and the heat resistor 6 to a constant state.

Now, the following description gives more detailed explanation regarding first fixation means 8.

First, the heat resistor 6 and the cooling block 5 are connected through the long screw 35. On this occasion, since the coil spring 37 is disposed between the lower face of the cooling block 5 and the nut 36, the elastic force of the coil spring 37 is transmitted to the long screw 35 through the bushing 39 and the nut 36. By this, the long screw 35 is always biased toward the other end side. Therefore, the heat resistor 6 is pulled to the cooling block 5 side, and pressed and fixed to the cooling block 5 while being biased by the constant elastic force as having been mentioned above.

And, by the repetitions of the heating and the cooling, even if the heat resistor 6 has distorted with respect to the cooling block 5 or the positional deviation and the like have occurred, the coil spring 37 expands and contracts in compliance with them, thereby absorbing the stress resulting from the distortion and the like. Therefore, as having been mentioned above, the fixation state between the heat resistor 6 and the cooling block 5 can be made constant.

Further, since the heat resistor 6 in the present embodiment is divided into four by the four slits toward the peripheral direction, the peripheral wall part 6b and the flange part 6c, which have been divided, becomes liable to distort respectively. In other words, the stress resulting from the distortion and the like is dispersed. And, since the long screws 35 are respectively fixed to the flange parts 6c having been divided into four, it is easy to certainly absorb the stress having been dispersed. As a result, the fixation state between the heat resistor 6 and the cooling block 5 can be made a constant state more certainly. Further, also the fact that the opening 6e of the flange part 6c, through which the long screw 35 is inserted, is formed in the long hole toward the radial direction contributes to absorb the stress resulting from the distortion and the like.

Additionally, the heat sink 2 in the present embodiment is fixed under the state having been pressed to the heat resistor 6 while being biased by the constant elastic force by the second fixation means 9. Therefore, by the difference in thermal expansion coefficient between the heat sink 2 and the heat resistor 6, even if the heat resistor 6 has been distorted with respect to the heat sink 2 or the positional deviation and the like have occurred, the stress resulting from these can be buffered by the elastic force. Therefore, similarly, it is possible to always maintain a fixation state between the heat sink 2 and the heat resistor 6 to a constant state.

Now, the following description gives more detailed explanation regarding this second fixation means 9.

First, the heat sink 2 and the base 31 are connection-fixed through the wire 40, the coil spring 43 and the fixation fitting 41. On this occasion, the coil spring 43 pulls the heat sink 2 through the wire 40. Therefore, the heat sink 2 is pressed and fixed to the heat resistor 6 while being biased by the constant elastic force as having been mentioned above.

And, by the repetitions of the heating and the cooling, even if the heat resistor 6 has distorted with respect to the heat sink 2 or the positional deviation and the like have occurred, the coil spring 43 expands and contracts in compliance with them, thereby absorbing the stress resulting from the distortion and the like. Therefore, as having been mentioned above, the fixation state between the heat resistor 6 and the cooling block 5 can be made constant.

Like this, even if the heating and the cooling are repeated, differing from conventional one, since the differential scanning calorimeter 1 of the present embodiment can maintain the fixation states between the heat resistor 6 and the heat sink 2 and between the heat resistor 6 and the cooling block 5 to the constant states, it is possible to stably maintain the heat flow path. As a result, it is possible to certainly obtain the heat flow difference signal having the reproducibility. Therefore, it is possible to highly precisely measure the sample to be measured, and the reliability can be improved.

Especially, since the coil spring 37 constituting the first fixation means 8 is made of the inconel, even if the temperature of the heat sink 2 has raised to about 400° C. by the heat from the heat sink 2, there is no fact that the mechanical property changes by the heat. Therefore, it is possible to bias the heat resistor 6 toward the cooling block 5 by the predetermined elastic force, and the reliability can be raised.

Further, since the bushing 38 made of the ceramic intervenes between the coil spring 37 and the cooling block 5, it is unnecessary that the coil spring 37 directly contacts with the cooling block 5. In other words, there is no fact that the heat is directly transmitted to the coil spring 37 from the cooling block 5, so that a temperature rise of the coil spring 37 can be prevented as much as possible. Therefore, it is possible to more certainly prevent the change in mechanical property of the coil spring 37 by an excessive heat. Further, since the heat influence on the coil spring 37 can be reduced as much as possible, it is possible to increase the selectivity of the material of the coil spring 37.

Additionally, since the first fixation means 8 can be constituted by the coil spring 37, the long screw 35, the nut 36 and the like without using a special mechanism, it is possible to intend to simplify the constitution, and it is possible to intend to reduce the cost.

Further, the coil spring 43 constituting the second fixation means 9 is connected to the heat sink 2 through the wire 40, and becomes a state having been separated from the heat sink 2 by a predetermined distance. Therefore, even if the heat sink 2 directly heated by the heater 3 has raised to about 725° C. for instance, there is no fact that this heat is directly transmitted to the coil spring 43, so that a temperature rise of the coil spring 43 can be prevented as much as possible. Therefore, similarly to the above coil spring 37, it is possible to prevent the change in mechanical property of the coil spring 43 by the excessive heat. Therefore, it is possible to bias the heat sink 2 toward the heat resistor 6 by the predetermined elastic force, and the reliability can be raised.

Further, similarly to the first fixation means 8, since the second fixation means 9 can be constituted by the coil spring 43, the wire 40 and the like without using a special mechanism, it is possible to intend to simplify the constitution, and it is possible to intend to reduce the cost.

Incidentally, a technical scope of the present invention is not limited to the above embodiment, and it is possible to add various modifications in a scope not deviating from a gist of the present invention.

For example, in the above embodiment, although the first fixation means and the second fixation means have been made the constitution having possessed both, the invention is not limited to this case, and at least one of these fixation means of may be included. With this construction, the fixation state of at least any one of between the heat resistor and the heat sink or between the heat resistor and the cooling block can be maintained to the constant state, and it is possible to stably maintain the heat flow path.

However, like the above embodiment, it is desirable to possess both the first fixation means and the second fixation means.

What is claimed is:

1. A differential scanning calorimeter comprising:
an accommodation chamber accommodating therein a sample to be measured and a reference material;
a heater attached so as to surround a periphery of the accommodation chamber to thereby heat the accommodation chamber;
a differential heat flow detector which is provided in the accommodation chamber, detects a temperature difference between the sample to be measured and the reference material, and outputs the temperature difference having been detected as a heat flow difference signal;
a cooling block which is disposed below the accommodation chamber while being separated by a constant distance, and cooling-controlled to a predetermined temperature;
a heat resistor, for controlling heat transfer, which is formed so as to have a predetermined heat resistance, interposed between the cooling block and the accommodation chamber to thereby mechanically connect both, and forms a heat flow path between the cooling block and the accommodation chamber;
a support means supporting the cooling block; and
a fixation means of at least any one between a first fixation means which fixes the heat resistor to the cooling block by pressing the former while being biased by a constant elastic force, and a second fixation means which fixes the accommodation chamber to the heat resistor by pressing the former while being biased by a constant elastic force.

2. A differential scanning calorimeter according to claim 1, wherein the first fixation means comprises a through-hole penetrating an upper face and a lower face of the cooling block, a shaft body which is movably inserted into the through-hole, whose one end is fixed to the heat resistor, and whose the other end protrudes to an outward of the cooling block from an inside of the through-hole, a nut meshed with the other end side of the shaft body, and a coil spring which is covered to the shaft body so as to surround a periphery of the shaft body under a state having been nipped between the nut and the cooling block, and biases the shaft body toward the other end side by an elastic force, the elastic force of the coil spring being made adjustable by moving the nut by a mesh in an axial direction of the shaft body.

3. A differential scanning calorimeter according to claim 2, wherein the coil spring is formed by a material made of a heat-resistant alloy.

4. A differential scanning calorimeter according to claim 2, wherein an annular bushing comprising ceramic is covered to the shaft body so as to surround the periphery of the shaft body under a state having been nipped between the coil spring and the cooling block.

5. A differential scanning calorimeter according to claim 1, wherein the second fixation means comprises an opening having been formed in the heat resistor, a second through-hole penetrating an upper face and a lower face of the cooling block, a second coil spring which is movably inserted into both the opening and the second through-hole, whose one end is fixed to the accommodation chamber, and whose the other end is fixed to the support means, thereby biasing the accommodation chamber toward the heat resistor by an elastic force, the second coil spring being fixed to the support means such that its own elastic force is adjustable.

6. A differential scanning calorimeter according to claim 5, wherein the accommodation chamber and the coil spring are fixed through a wire material having a heat resistance, and between the accommodation chamber and the coil spring there is separated by a predetermined distance.

* * * * *